United States Patent [19]

Wingert et al.

[11] Patent Number: 5,089,528
[45] Date of Patent: Feb. 18, 1992

[54] SULFUR-CONTAINING OXIME ETHERS AND FUNGICIDES CONTAINING THEM

[75] Inventors: Horst Wingert, Mannheim; Siegbert Brand, Weinheim; Bernd Wenderoth, Lampertheim; Franz Schuetz, Ludwigshafen; Hubert Sauter, Mannheim; Franz Roehl, Ludwigshafen; Gisela Lorenz, Neustadt; Eberhard Ammermann, Ludwigshafen, all of

[73] Assignee: Basf Aktiengesellschaft, Ludwigshafen, Fed. Rep. of Germany

[21] Appl. No.: 436,804

[22] Filed: Nov. 15, 1989

[30] Foreign Application Priority Data

Dec. 23, 1988 [DE] Fed. Rep. of Germany ....... 3843439

[51] Int. Cl.$^5$ .................... A01N 33/24; C07C 749/01
[52] U.S. Cl. .................................. 514/640; 564/256; 564/265
[58] Field of Search ................ 564/256, 265; 514/640

[56] References Cited

FOREIGN PATENT DOCUMENTS 253213 1/1988 European Pat. Off. .
254426 1/1988 European Pat. Off. .
0299694 1/1989 European Pat. Off. .

*Primary Examiner*—Jane T. Fan
*Assistant Examiner*—Raymond Covington
*Attorney, Agent, or Firm*—Oblon, Spivak, McClelland, Maier & Neustadt

[57] ABSTRACT

Oxime ether derivatives of the formula

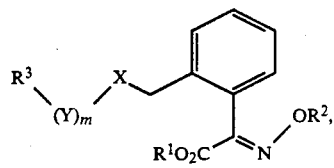

where $R^1$ and $R^2$ are each hydrogen or alkyl, X is S, SO or $SO_2$, $R^3$ is hydrogen, cycloalkyl, phenyl, naphthyl, quinolinyl or phenanthrenyl, these radicals being unsubstituted or substituted, Y is alkylene, alkenylene or alkynylene, and m is 0 or 1.

7 Claims, No Drawings

SULFUR-CONTAINING OXIME ETHERS AND FUNGICIDES CONTAINING THEM

The present invention relates to novel oxime ether derivatives, their preparation, fungicides containing these derivatives and their use as fungicides.

It is known that oxime ethers, for example methyl 2-(phenoxymethyl)-phenylglyoxylate O-methyloxime, can be used as fungicides (European Patents 253,213 and 254,426). However, their fungicidal action is frequently insufficient.

We have found that substituted oxime ether derivatives of the formula

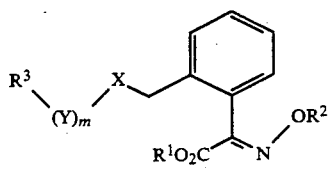

I where $R^1$ and $R^2$ are each hydrogen or $C_1$-$C_5$, X is S, SO or $SO_2$, $R^3$ is hydrogen, $C_3$-$C_8$-cycloalkyl, phenyl, naphthyl, quinolyl or phenanthrenyl, and these radicals are unsubstituted or substituted by halogen, cyano, nitro, formyl, $C_1$-$C_{10}$-alkyl, $C_1$-$C_4$-alkoxy, $C_1$- or $C_2$-haloalkyl, aryl or $C_1$-$C_4$-alkoxycarbonyl, Y is a straight-chain or branched a , alkenylene or alkynylene radical and m is 0 or 1, have an excellent fungicidal action.

The radicals stated for the general formula I may have, for example, the following meanings: $R^1$ and $R^2$ are identical or different and are each, for example, hydrogen or $C_1$-$C_5$-alkyl, such as methyl, ethyl, propyl, isopropyl, butyl or pentyl, preferably methyl.

X may be S, SO or $SO_2$, S being preferred $R^3$ may be, for example, hydrogen $C_3$-$C_8$-cycloalkyl (e.g. cyclopropyl, cyclobutyl, cyclopentyl, cyclohexyl, cycloheptyl or cyclooctyl) or phenyl, naphthyl, quinolyl or phenanthrenyl, and the rings may be unsubstituted or substituted by one to three of the following radicals, which may be identical or different: halogen (e.g. fluorine, chlorine or bromine), cyano, nitro, formyl, $C_1$-$C_{10}$-alkyl (eg. methyl, ethyl, n-propyl, isopropyl, n-butyl, isobutyl, sec-butyl, tert-butyl, n-pentyl, isopentyl, sec-pentyl, tert-pentyl, neopentyl, hexyl, heptyl, octyl, nonyl or decyl), $C_1$- or $C_2$-haloalkyl (e.g. difluoromethyl, trifluoromethyl, chloromethyl, dichloromethyl, trichloromethyl or pentafluoroethyl), $C_1$-$C_4$-alkoxy (e.g. methoxy, ethoxy, n-propoxy, isopropoxy, n-butoxy, isobutoxy, sec-butoxy or tert-butoxy), aryl (e.g. phenyl, naphthyl or pyridyl), $C_1$-$C_4$-alkoxycarbonyl (e.g. methoxycarbonyl, ethoxycarbonyl, propoxycarbonyl or butoxycarbonyl).

Y may be, for example, $C_1$-$C_{10}$-alkylene, such as methylene, ethylene, n-propylene, isopropylene, n-butylene, isobutylene, sec-butylene, tert-butylene, n-pentylene, isopentylene, sec-pentylene, tert-pentylene, neopentylene, hexylene, heptylene, octylene, nonylene or decylene, $C_2$- or $C_3$-alkylene, such as vinylene or allylene, methylene being preferred.

m may be 0 or 1.

Because of the C=N double bond, the novel compounds of the formula I may be obtained in their preparation in the form of E/Z isomer mixtures, which can be separated into the individual components in a conventional manner, for example by crystallization or chromatography. The invention relates to both the individual isomeric compounds and their mixtures, and both the said compounds and the said mixtures can be used as fungicides.

The novel compounds of the general formula I where X is S can be prepared, for example, by reacting a thiol of the formula (II) with a benzyl halide of the general formula III, where Hal is Cl, Br or I.

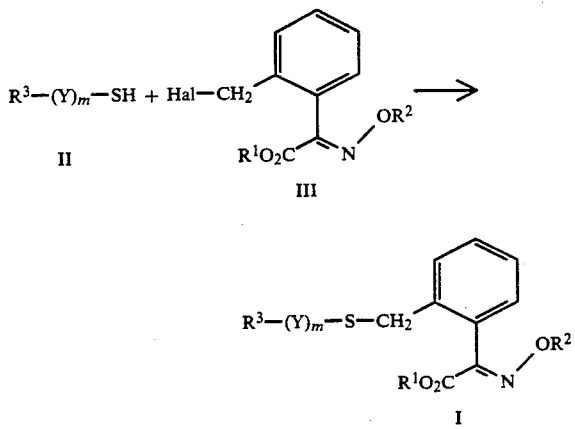

The reactions to give the compounds of the formula I can be carried out, for example, in an inert solvent or diluent (e.g. acetone, acetonitrile, dimethyl sulfoxide, dioxane, dimethylformamide, N-methylpyrrolidone, N,N'-dimethylpropyleneurea or pyridine) using a base (e.g. sodium carbonate or potassium carbonate). It may also be advantageous to add a catalyst, such as tris-(3,6-dioxoheptyl)-amine to the reaction mixture (J. Org. Chem. 50 (1985), 3717).

Alternatively, the compounds of the general formula II can first be converted with a base (e.g. sodium hydroxide or potassium hydroxide) into the corresponding sodium or potassium salts and the latter then reacted with the benzyl halides of the formula III in an inert solvent or diluent (e.g. dimethylformamide) to give the corresponding compounds of the general formula I.

The thiols of the general formula $R^3$-$(Y)_m$-SH (where $R^3$, Y and m have the abovementioned meanings) are either known or can be prepared by processes similar to known processes. Appropriate preparation processes are described in, for example, Houben-Weyl, Methoden der organischen Chemie, VI/3, page 54 et seq. (1965).

The ortho-substituted benzyl halides of the formula III can be prepared by halogenating α-ketocarboxylates of the formula IV which are known from the literature (cf. J. M. Photis, Tetrahedron Lett. 1980, 3539) at the methyl group by methods known from the literature to give the halides of the formula V.

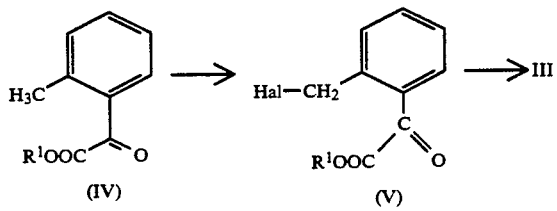

For example, α-ketonecarboxylates of the general formula V, where $R^1$ have the abovementioned meanings, are obtained using bromine or chlorine in a solvent, such as tetrachloromethane, if necessary with exposure to a light source (for example an Hg vapor lamp, 300 W) or using N-chloro- or N-bromosuccinimide (Horner and Winkelmann, Angew. Chem. 71 (1959), 349).

The halides of the formula III can be prepared by reacting an α-ketocarboxylate of the formula V, for example, a) with an O-substituted hydroxylamine of the formula $H_2N-OR^2$, where $R^2$ has the abovementioned meanings, or b) with hydroxylamine to give the corresponding oxime and then with an alkyl halide of the formula $R^2$-Hal, where $R^2$ has the abovementioned meanings and Hal is halogen (F, Cl, Br or I), or with a dialkyl sulfate.

The novel compounds of the formula I (where X is SO or $SO_2$) are obtained by oxidation of the corresponding thioethers of the general formula I (where X is S). The oxidation can be carried out, for example, using peroxo compounds, for example meta-chloroperbenzoic acid, in an inert solvent, such as toluene The compounds of the formula VI can be converted into the halides of the formula III by halogenation at the methyl group by methods known from the literature This is achieved, for example, using bromine or chlorine in a solvent, such as tetrachloromethane, if necessary with exposure to a light source (for example an Hg vapor lamp, 300 W) or using N-chloro- or N-bromosuccinimide (Horner and Winkelmann, Angew. Chem. 71 (1959), 349).

The novel compounds of the formula I where X is S can also be prepared, for example, by reacting the novel α-ketocarboxylates of the formula VII

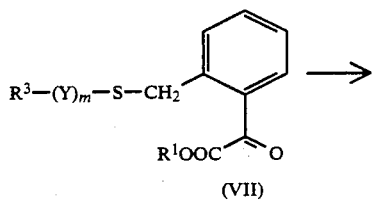

(VII)

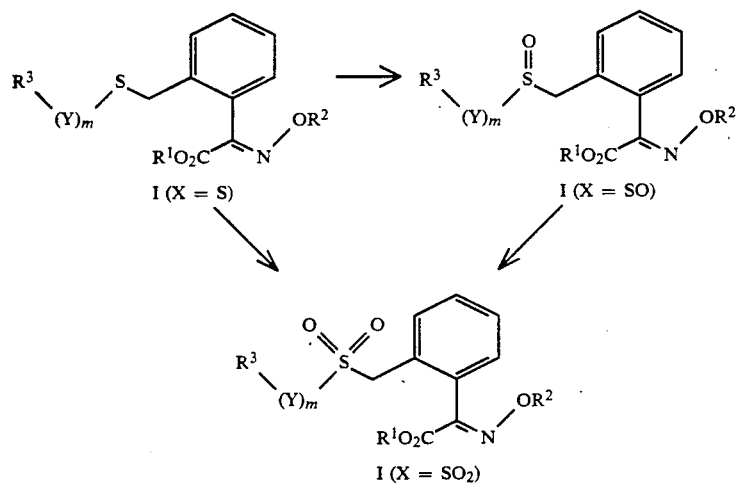

(cf. for example Houben-Weyl, Methoden der Org. Chemie IX, 213, 228 (1955)).

The halides of the formula III can also be prepared by reacting an α-ketocarboxylate of the formula IV, for example, a) with an O-substituted hydroxylamine of the formula $H_2N-OR^2$, where $R^2$ has the abovementioned meanings, or b) with hydroxylamine to give the corresponding oxime and then with an alkyl halide of the formula $R^2$-Hal, where $R^2$ has the abovementioned meanings and Hal is halogen (F, Cl, Br or I), or with a dialkyl sulfate to give oxime ether derivatives of the general formula VI, where $R^1$ and $R^2$ each have the abovementioned meanings.

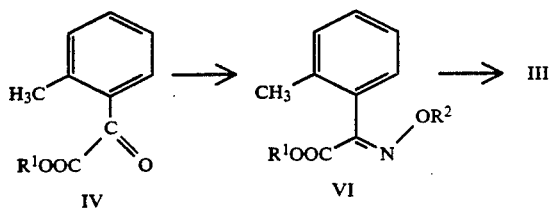

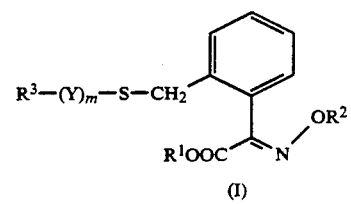

(I)

a) with an O-substituted hydroxylamine of the formula $H_2NOR^2$, where $R^2$ has the abovementioned meanings, or b) with hydroxylamine to give the corresponding oxime and then with an alkyl halide of the formula $R^2$-Hal, where $R^2$ has the abovementioned meanings and Hal is halogen (F, Cl, Br or I), or with a dialkyl sulfate.

The novel α-ketocarboxylates of the general formula VII are useful intermediates. They can be prepared, for example, by reacting the abovementioned compound of the formula V with a thiol of the general formula II.

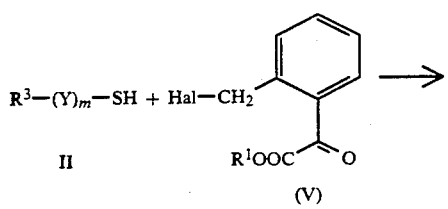

(V)

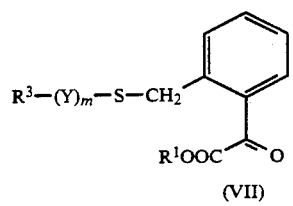

(VII)

The reactions to give the compounds of the formula VII can be carried out, for example, in an inert solvent or diluent (e.g. acetone, acetonitrile, dimethyl sulfoxide, dioxane, dimethylformamide, N-methylpyrrolidone, N,N'-dimethylpropyleneurea or pyridine) using a base (e.g. sodium carbonate or potassium carbonate). It may also be advantageous to add a catalyst, such as tris-(3,6-dioxoheptyl)-amine, to the reaction mixture (J. Org. Chem. 50 (1985), 3717).

Alternatively, the compounds of the general formula II can be first converted with a base (e.g. sodium hydroxide or potassium hydroxide) into the corresponding sodium or potassium salts and the latter then reacted with the benzyl halides of the formula V in an inert solvent or diluent (e.g. dimethylformamide) to give the novel α-ketocarboxylates of the general formula VII.

EXAMPLES

The Examples which follow illustrate the preparation of the novel active ingredients of the general formula I.

Method 1

Preparation of methyl 2-(bromomethyl)-phenylglyoxylate 5.34 g (30 millimoles) of methyl 2-methylphenylglyoxylate and 5.34 g (30 millimoles) of N-bromosuccinimide in 1,000 l of tetrachloromethane are exposed for one hour to a 300 W Hg vapor lamp. Thereafter, the organic phase is washed once with water and three times with sodium bicarbonate solution and dried over sodium sulfate/sodium carbonate. After the organic phase has been evaporated down, the crude product is chromatographed over silica gel using 1:9 methyl tert-butyl ether/n-hexane. 3.8 g (49%) of the abovementioned compound are obtained as a yellow oil. $^1$H-NMR (CDCl$_3$): δ=3.97 (s, 3H); 4.90 (s, 2H); 7.4–7.8 (m, 4H)

IR (film): 0 2955, 1740, 1689, 1435, 1318, 1207, 999 cm$^{-1}$

Method 2

Preparation of methyl 2-(chloromethyl)-phenylglyoxylate 100 g (0.56 mole) of methyl 2-methylphenylglyoxylate in 600 ml of tetrachloromethane are initially taken. The mixture is refluxed with exposure to a 300 W Hg vapor lamp, and 28 g (0.39 mole) of chlorine gas are passed in during this procedure. After a conversion of about 50% (checked by thin layer chromatography), the reaction is terminated, the mixture is evaporated down and the residue is subjected to fractional distillation. The substance is obtained as a yellow oil.

$^1$H-NMR (CDCl$_3$): δ=3.97 (s, 3H), 5.0 (s, 2H); 7.4–7.8 (m, 4H)

Method 3

Preparation of methyl 2-(bromomethyl)-phenylglyoxylate O-methyloxime 21.4 g (0.133 mole) of bromine are added to 27.5 g (0.133 mole) of methyl 2-methylphenylglyoxylate O-methyloxime, dissolved in 400 ml of tetrachloromethane, while stirring. The mixture is then refluxed for four hours with exposure to a 300 W Hg vapor lamp. It is then evaporated down, the residue is taken up in ethyl acetate/water and the solution is washed with H$_2$O, dried with sodium sulfate and evaporated down. The crude product is purified by chromatography over silica gel using 9:1 cyclohexane/ethyl acetate. 17.4 g (46%) of the abovementioned compound are obtained as an oil.

$^1$H-NMR (CDCl$_3$): δ=3.88 (s, 3H); 4.08 (s, 3H); 4.33 (s, 2H); 6.12–7.52 (m, 4H)

EXAMPLE 1

Preparation of methyl 2-(phenylthiomethyl-)-phenylglyoxylate O-methyloxime (compound 57 in Table 1)

1.5 g (0.014 mole) of thiophenol and 4 g (0.014 mole) of methyl 2-(bromomethyl)-phenylglyoxylate O-methyloxime (Method 3) are dissolved in 100 ml of acetone. 2.2 g of potassium carbonate and 0.1 g of potassium iodide are added. The stirred mixture is refluxed for 17 hours and then cooled, after which 100 ml of water are added. The aqueous phase is extracted with methylene chloride and the extract is dried over sodium sulfate and evaporated down. The crude product is crystallized by trituration with n-pentane. 2.33 g (55%) of the abovementioned compound are obtained as a colorless solid (mp.=60°–65° C.)

$^1$H-NMR (CDCl$_3$/TMS): δ=3.86 (s, 3H; 3.95 (s, 2H); 4.04 (s, 3H); 7.12–7.31 ppm (m, 9H).

The compounds listed in Table 1 can be synthesized by appropriate modification of the above information.

TABLE 1

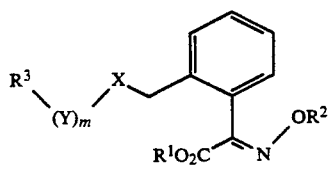

| No. | X | (Y)$_m$ | m | R$^3$ | R$^1$ | R$^2$ | IR (cm$^{-1}$) | mp |
|-----|---|---------|---|-------|-------|-------|----------------|-----|
| 1 | S | CH$_2$ | 1 | H | CH$_3$ | CH$_3$ | | |
| 2 | S | CH$_2$ | 1 | CH$_3$ | CH$_3$ | CH$_3$ | | |

TABLE 1-continued

| No. | X | (Y)$_m$ | m | R$^3$ | R$^1$ | R$^2$ | IR (cm$^{-1}$) mp |
|---|---|---|---|---|---|---|---|
| 3 | S | (CH$_2$)$_2$ | 1 | CH$_3$ | CH$_3$ | CH$_3$ | |
| 4 | S | (CH$_2$)$_3$ | 1 | CH$_3$ | CH$_3$ | CH$_3$ | |
| 5 | S | (CH$_2$)$_4$ | 1 | CH$_3$ | CH$_3$ | CH$_3$ | |
| 6 | S | (CH$_2$)$_5$ | 1 | CH$_3$ | CH$_3$ | CH$_3$ | |
| 7 | S | (CH$_2$)$_6$ | 1 | CH$_3$ | CH$_3$ | CH$_3$ | |
| 8 | S | (CH$_2$)$_7$ | 1 | CH$_3$ | CH$_3$ | CH$_3$ | |
| 9 | S | (CH$_2$)$_8$ | 1 | CH$_3$ | CH$_3$ | CH$_3$ | |
| 10 | S | (CH$_2$)$_9$ | 1 | CH$_3$ | CH$_3$ | CH$_3$ | |
| 11 | S | CH(i-Pr) | 1 | CH$_3$ | CH$_3$ | CH$_3$ | |
| 12 | S | CH(CH$_3$) | 1 | CH$_3$ | CH$_3$ | CH$_3$ | |
| 13 | S | CH(Et) | 1 | CH$_3$ | CH$_3$ | CH$_3$ | |
| 14 | S | CH(Pr) | 1 | CH$_3$ | CH$_3$ | CH$_3$ | |
| 15 | S | CH$_2$ | 1 | cyclopropyl | CH$_3$ | CH$_3$ | |
| 16 | S | CH$_2$ | 1 | cyclohexyl | CH$_3$ | CH$_3$ | |
| 17 | S | — | 0 | cyclopentyl | CH$_3$ | CH$_3$ | |
| 18 | S | — | 0 | cyclohexyl | CH$_3$ | CH$_3$ | |
| 19 | S | — | 0 | cyclooctyl | CH$_3$ | CH$_3$ | |
| 20 | S | CH$_2$ | 1 | 1-naphthyl | CH$_3$ | CH$_3$ | |
| 21 | S | CH(CH$_3$) | 1 | phenyl | CH$_3$ | CH$_3$ | |
| 22 | S | CH$_2$ | 1 | CH=CH$_2$ | CH$_3$ | CH$_3$ | |
| 23 | S | CH$_2$ | 1 | C(CH$_3$)=CH$_2$ | CH$_3$ | CH$_3$ | |
| 24 | S | CH$_2$ | 1 | 2-chlorophenyl | CH$_3$ | CH$_3$ | |
| 25 | S | CH$_2$ | 1 | 3-chlorophenyl | CH$_3$ | CH$_3$ | |
| 26 | S | CH$_2$ | 1 | 4-chlorophenyl | CH$_3$ | CH$_3$ | |
| 27 | S | CH$_2$ | 1 | 2-bromophenyl | CH$_3$ | CH$_3$ | |
| 28 | S | CH$_2$ | 1 | 3-bromophenyl | CH$_3$ | CH$_3$ | |
| 29 | S | CH$_2$ | 1 | 4-bromophenyl | CH$_3$ | CH$_3$ | |
| 30 | S | CH$_2$ | 1 | 2-fluorophenyl | CH$_3$ | CH$_3$ | |
| 31 | S | CH$_2$ | 1 | 3-fluorophenyl | CH$_3$ | CH$_3$ | |
| 32 | S | CH$_2$ | 1 | 4-fluorophenyl | CH$_3$ | CH$_3$ | |
| 33 | S | CH$_2$ | 1 | 2-methylphenyl | CH$_3$ | CH$_3$ | |
| 34 | S | CH$_2$ | 1 | 3-methylphenyl | CH$_3$ | CH$_3$ | |
| 35 | S | CH$_2$ | 1 | 4-methylphenyl | CH$_3$ | CH$_3$ | |
| 36 | S | CH$_2$ | 1 | 4-dodecylphenyl | CH$_3$ | CH$_3$ | |
| 37 | S | CH$_2$ | 1 | 2-nitrophenyl | CH$_3$ | CH$_3$ | |
| 38 | S | CH$_2$ | 1 | 3-nitrophenyl | CH$_3$ | CH$_3$ | |
| 39 | S | CH$_2$ | 1 | 4-nitrophenyl | CH$_3$ | CH$_3$ | |
| 40 | S | CH$_2$ | 1 | 2-methoxyphenyl | CH$_3$ | CH$_3$ | |
| 41 | S | CH$_2$ | 1 | 3-methoxyphenyl | CH$_3$ | CH$_3$ | |
| 42 | S | CH$_2$ | 1 | 4-methoxyphenyl | CH$_3$ | CH$_3$ | |
| 43 | S | CH$_2$ | 1 | 2-trifluoromethylphenyl | CH$_3$ | CH$_3$ | |
| 44 | S | CH$_2$ | 1 | 3-trifluoromethylphenyl | CH$_3$ | CH$_3$ | |
| 45 | S | CH$_2$ | 1 | 4-trifluoromethylphenyl | CH$_3$ | CH$_3$ | |
| 46 | S | CH$_2$ | 1 | 2,4-dichlorophenyl | CH$_3$ | CH$_3$ | |
| 47 | S | CH$_2$ | 1 | 3,4-dichlorophenyl | CH$_3$ | CH$_3$ | |
| 48 | S | CH$_2$ | 1 | 2-chloro, 6-fluorophenyl | CH$_3$ | CH$_3$ | |
| 49 | S | CH$_2$ | 1 | 3,4-dimethylphenyl | CH$_3$ | CH$_3$ | |
| 50 | S | CH$_2$CH$_2$ | 1 | phenyl | CH$_3$ | CH$_3$ | |
| 51 | S | CH$_2$CH$_2$CH$_2$ | 1 | phenyl | CH$_3$ | CH$_3$ | |
| 52 | S | CH$_2$CH$_2$CH$_2$CH$_2$ | 1 | 4-chlorophenyl | CH$_3$ | CH$_3$ | |
| 53 | S | — | 0 | 1-naphthyl | CH$_3$ | CH$_3$ | |
| 54 | S | — | 0 | 2-naphthyl | CH$_3$ | CH$_3$ | 77–80° C. |
| 55 | S | — | 0 | 3-phenathrenyl | CH$_3$ | CH$_3$ | |
| 56 | S | — | 0 | 8-quinolinyl | CH$_3$ | CH$_3$ | |
| 57 | S | — | 0 | phenyl | CH$_3$ | CH$_3$ | 1727, 1480, 1438, 1321, 1218, 1967, 1045, 1018, 958, 743 |
| 58 | S | — | 0 | 2-chlorophenyl | CH$_3$ | CH$_3$ | 1740, 1452, 1431, 1307, 1219, 1066, 1047, 1008, 979, 743 |
| 59 | S | — | 0 | 3-chlorophenyl | CH$_3$ | CH$_3$ | 1727, 1580, 1467, 1217, 1088, 1061, 1010, 960, 777, 771 |
| 60 | S | — | 0 | 4-chlorophenyl | CH$_3$ | CH$_3$ | 82–85° C. |
| 61 | S | — | 0 | 2-bromophenyl | CH$_3$ | CH$_3$ | |
| 62 | S | — | 0 | 3-bromophenyl | CH$_3$ | CH$_3$ | |
| 63 | S | — | 0 | 4-bromophenyl | CH$_3$ | CH$_3$ | |
| 64 | S | — | 0 | 2-fluorophenyl | CH$_3$ | CH$_3$ | |
| 65 | S | — | 0 | 3-fluorophenyl | CH$_3$ | CH$_3$ | |
| 66 | S | — | 0 | 4-fluorophenyl | CH$_3$ | CH$_3$ | 1727, 1588, 1490, 1307, 1223, 1069, 1011, 982, 771, 761 |
| 67 | S | — | 0 | 2-methylphenyl | CH$_3$ | CH$_3$ | 1735, 1448, 1433, 1297, 1226, 1066, 1008, 980, 763, 748 |
| 68 | S | — | 0 | 3-methylphenyl | CH$_3$ | CH$_3$ | 39–40° C. |
| 69 | S | — | 0 | 4-Methylphenyl | CH$_3$ | CH$_3$ | 68–71° C. |

TABLE 1-continued $$\text{structure: phenyl ring with } R^3(Y)_m\text{-CH}_2\text{-X-CH}_2\text{- substituent ortho to } C(=NOR^2)(CO_2R^1)$$

| No. | X | (Y)ₘ | m | R³ | R¹ | R² | IR (cm⁻¹) mp |
|---|---|---|---|---|---|---|---|
| 70 | S | — | 0 | 2-ethylphenyl | CH₃ | CH₃ | |
| 71 | S | — | 0 | 3-ethylphenyl | CH₃ | CH₃ | |
| 72 | S | — | 0 | 4-ethylphenyl | CH₃ | CH₃ | |
| 73 | S | — | 0 | 2-isopropylphenyl | CH₃ | CH₃ | 53–55° C. |
| 74 | S | — | 0 | 3-isopropylphenyl | CH₃ | CH₃ | |
| 75 | S | — | 0 | 4-isopropylphenyl | CH₃ | CH₃ | |
| 76 | S | — | 0 | 2-tert-butylphenyl | CH₃ | CH₃ | |
| 77 | S | — | 0 | 3-tert-butylphenyl | CH₃ | CH₃ | |
| 78 | S | — | 0 | 4-tert-butylphenyl | CH₃ | CH₃ | 80–83° C. |
| 79 | S | — | 0 | 4-butylphenyl | CH₃ | CH₃ | |
| 80 | S | — | 0 | 4-hexylphenyl | CH₃ | CH₃ | |
| 81 | S | — | 0 | 4-nonylphenyl | CH₃ | CH₃ | |
| 82 | S | — | 0 | 4-decylphenyl | CH₃ | CH₃ | |
| 83 | S | — | 0 | 2-methoxyphenyl | CH₃ | CH₃ | 1727, 1476, 1462, 1434, 1245, 1218, 1068, 1043, 1019, 753 |
| 84 | S | — | 0 | 3-methoxyphenyl | CH₃ | CH₃ | 60–64° C. |
| 85 | S | — | 0 | 4-methoxyphenyl | CH₃ | CH₃ | 1727, 1591, 1494, 1439, 1298, 1285, 1246, 1217, 1067, 1018 |
| 86 | S | — | 0 | 2-trifluoromethylphenyl | CH₃ | CH₃ | |
| 87 | S | — | 0 | 3-trifluoromethylphenyl | CH₃ | CH₃ | 60–63° C. |
| 88 | S | — | 0 | 4-trifluoromethylphenyl | CH₃ | CH₃ | |
| 89 | S | — | 0 | 4-formylphenyl | CH₃ | CH₃ | |
| 90 | S | — | 0 | 2-nitrophenyl | CH₃ | CH₃ | |
| 91 | S | — | 0 | 3-nitrophenyl | CH₃ | CH₃ | |
| 92 | S | — | 0 | 4-nitrophenyl | CH₃ | CH₃ | |
| 93 | S | — | 0 | 2,5-dichlorophenyl | CH₃ | CH₃ | 87–93° C. |
| 94 | S | — | 0 | 2,6-dichlorophenyl | CH₃ | CH₃ | 113–117° C. |
| 95 | S | — | 0 | 3,4-dichlorophenyl | CH₃ | CH₃ | |
| 96 | S | — | 0 | 2,3-dichlorophenyl | CH₃ | CH₃ | |
| 97 | S | — | 0 | 2,4-dichlorophenyl | CH₃ | CH₃ | |
| 98 | S | — | 0 | 3,5-dichlorophenyl | CH₃ | CH₃ | |
| 99 | S | — | 0 | 2,3,4-trichlorophenyl | CH₃ | CH₃ | 114–118° C. |
| 100 | S | — | 0 | 2,4,5-trichlorophenyl | CH₃ | CH₃ | 121–124° C. |
| 101 | S | — | 0 | 2,4,6-trichlorophenyl | CH₃ | CH₃ | |
| 102 | S | — | 0 | 2,3,4,6-tetrachlorophenyl | CH₃ | CH₃ | |
| 103 | S | — | 0 | 2,3,4,5,6-pentachlorophenyl | CH₃ | CH₃ | |
| 104 | S | — | 0 | 2,3,4,5-tetrafluorophenyl | CH₃ | CH₃ | |
| 105 | S | — | 0 | 2,3,5,6-tetrafluorophenyl | CH₃ | CH₃ | |
| 106 | S | — | 0 | 2,3,4,5,6-pentafluorophenyl | CH₃ | CH₃ | |
| 107 | S | — | 0 | 2-chloro, 4-fluorophenyl | CH₃ | CH₃ | |
| 108 | S | — | 0 | 3-chloro, 4-fluorophenyl | CH₃ | CH₃ | |
| 109 | S | — | 0 | 2-chloro, 6-methylphenyl | CH₃ | CH₃ | |
| 110 | S | — | 0 | 4-chloro, 2-methylphenyl | CH₃ | CH₃ | |
| 111 | S | — | 0 | 2,4-dichloro, 5-methylphenyl | CH₃ | CH₃ | |
| 112 | S | — | 0 | 4-chloro, 2,5-dimethylphenyl | CH₃ | CH₃ | |
| 113 | S | — | 0 | 4-bromo, 3-methylphenyl | CH₃ | CH₃ | |
| 114 | S | — | 0 | 3,5-bistrifluoromethylphenyl | CH₃ | CH₃ | |
| 115 | S | — | 0 | 2,5-dimethylphenyl | CH₃ | CH₃ | |
| 116 | S | — | 0 | 2,4-dimethylphenyl | CH₃ | CH₃ | |
| 117 | S | — | 0 | 2,5-dimethylphenyl | CH₃ | CH₃ | |
| 118 | S | — | 0 | 2,6-dimethylphenyl | CH₃ | CH₃ | |
| 119 | S | — | 0 | 3,4-dimethylphenyl | CH₃ | CH₃ | |
| 120 | S | — | 0 | 3,5-dimethylphenyl | CH₃ | CH₃ | |
| 121 | S | — | 0 | 2,4,5-trimethylphenyl | CH₃ | CH₃ | |
| 122 | S | — | 0 | 2,6-diethylphenyl | CH₃ | CH₃ | |
| 123 | S | — | 0 | 2,4-di-tert.-butylphenyl | CH₃ | CH₃ | |
| 124 | S | — | 0 | 2,5-dimethoxyphenyl | CH₃ | CH₃ | |
| 125 | S | — | 0 | 3,4-dimethoxyphenyl | CH₃ | CH₃ | |
| 126 | S | — | 0 | 2-methyl, 4-tert.-butylphenyl | CH₃ | CH₃ | 2963, 2953, 1728, 1481, 1437, 1320 1217, 1067, 1045, 1018 |
| 127 | S | — | 0 | 2-methoxycarbonylphenyl | CH₃ | CH₃ | |
| 128 | S | — | 0 | 2-ethoxycarbonylphenyl | CH₃ | CH₃ | |
| 129 | S | — | 0 | 2-propoxycarbonylphenyl | CH₃ | CH₃ | |
| 130 | S | — | 0 | 2-butoxycarbonylphenyl | CH₃ | CH₃ | |
| 131 | S | — | 0 | 2-cyanophenyl | CH₃ | CH₃ | |
| 132 | S | — | 0 | 3-cyanophenyl | CH₃ | CH₃ | |
| 133 | S | — | 0 | 4-cyanophenyl | CH₃ | CH₃ | |
| 134 | S | — | 0 | phenyl | CH₃ | Et | |
| 135 | S | — | 0 | phenyl | Et | CH₃ | |
| 136 | S | — | 0 | phenyl | CH₃ | n-Bu | |

TABLE 1-continued

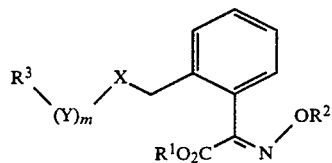

| No. | X | (Y)$_m$ | m | R$^3$ | R$^1$ | R$^2$ | IR (cm$^{-1}$) mp |
|---|---|---|---|---|---|---|---|
| 137 | S | — | 0 | phenyl | n-Bu | n-Bu | |

TABLE 2

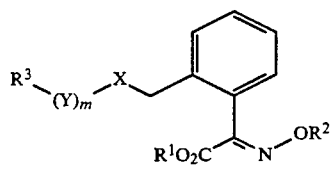

| No. | X | (Y)$_m$ | m | R$^3$ | R$^1$ | R$^2$ | IR (cm$^{-1}$) |
|---|---|---|---|---|---|---|---|
| 1 | SO | CH$_2$ | 1 | H | CH$_3$ | CH$_3$ | |
| 2 | SO | CH$_2$ | 1 | CH$_3$ | CH$_3$ | CH$_3$ | |
| 3 | SO | (CH$_2$)$_2$ | 1 | CH$_3$ | CH$_3$ | CH$_3$ | |
| 4 | SO | (CH$_2$)$_3$ | 1 | CH$_3$ | CH$_3$ | CH$_3$ | |
| 5 | SO | (CH$_2$)$_4$ | 1 | CH$_3$ | CH$_3$ | CH$_3$ | |
| 6 | SO | (CH$_2$)$_5$ | 1 | CH$_3$ | CH$_3$ | CH$_3$ | |
| 7 | SO | (CH$_2$)$_6$ | 1 | CH$_3$ | CH$_3$ | CH$_3$ | |
| 8 | SO | (CH$_2$)$_7$ | 1 | CH$_3$ | CH$_3$ | CH$_3$ | |
| 9 | SO | (CH$_2$)$_8$ | 1 | CH$_3$ | CH$_3$ | CH$_3$ | |
| 10 | SO | (CH$_2$)$_9$ | 1 | CH$_3$ | CH$_3$ | CH$_3$ | |
| 11 | SO | CH(i-Pr) | 1 | CH$_3$ | CH$_3$ | CH$_3$ | |
| 12 | SO | CH(CH$_3$) | 1 | CH$_3$ | CH$_3$ | CH$_3$ | |
| 13 | SO | CH(Et) | 1 | CH$_3$ | CH$_3$ | CH$_3$ | |
| 14 | SO | CH(Pr) | 1 | CH$_3$ | CH$_3$ | CH$_3$ | |
| 15 | SO | CH$_2$ | 1 | cyclopropyl | CH$_3$ | CH$_3$ | |
| 16 | SO | CH$_2$ | 1 | cyclohexyl | CH$_3$ | CH$_3$ | |
| 17 | SO | — | 0 | cyclopentyl | CH$_3$ | CH$_3$ | |
| 18 | SO | — | 0 | cyclohexyl | CH$_3$ | CH$_3$ | |
| 19 | SO | — | 0 | cyclooctyl | CH$_3$ | CH$_3$ | |
| 20 | SO | CH$_2$ | 1 | 1-naphthyl | CH$_3$ | CH$_3$ | |
| 21 | SO | CH(CH$_3$) | 1 | phenyl | CH$_3$ | CH$_3$ | |
| 22 | SO | CH$_2$ | 1 | CH=CH$_2$ | CH$_3$ | CH$_3$ | |
| 23 | SO | CH$_2$ | 1 | C(CH$_3$)=CH$_2$ | CH$_3$ | CH$_3$ | |
| 24 | SO | CH$_2$ | 1 | 2-chlorophenyl | CH$_3$ | CH$_3$ | |
| 25 | SO | CH$_2$ | 1 | 3-chlorophenyl | CH$_3$ | CH$_3$ | |
| 26 | SO | CH$_2$ | 1 | 4-chlorophenyl | CH$_3$ | CH$_3$ | |
| 27 | SO | CH$_2$ | 1 | 2-bromophenyl | CH$_3$ | CH$_3$ | |
| 28 | SO | CH$_2$ | 1 | 3-bromophenyl | CH$_3$ | CH$_3$ | |
| 29 | SO | CH$_2$ | 1 | 4-bromophenyl | CH$_3$ | CH$_3$ | |
| 30 | SO | CH$_2$ | 1 | 2-fluorophenyl | CH$_3$ | CH$_3$ | |
| 31 | SO | CH$_2$ | 1 | 3-fluorophenyl | CH$_3$ | CH$_3$ | |
| 32 | SO | CH$_2$ | 1 | 4-fluorophenyl | CH$_3$ | CH$_3$ | |
| 33 | SO | CH$_2$ | 1 | 2-methylphenyl | CH$_3$ | CH$_3$ | |
| 34 | SO | CH$_2$ | 1 | 3-methylphenyl | CH$_3$ | CH$_3$ | |
| 35 | SO | CH$_2$ | 1 | 4-methylphenyl | CH$_3$ | CH$_3$ | |
| 36 | SO | CH$_2$ | 1 | 4-dodecylphenyl | CH$_3$ | CH$_3$ | |
| 37 | SO | CH$_2$ | 1 | 2-nitrophenyl | CH$_3$ | CH$_3$ | |
| 38 | SO | CH$_2$ | 1 | 3-nitrophenyl | CH$_3$ | CH$_3$ | |
| 39 | SO | CH$_2$ | 1 | 4-nitrophenyl | CH$_3$ | CH$_3$ | |
| 40 | SO | CH$_2$ | 1 | 2-methoxyphenyl | CH$_3$ | CH$_3$ | |
| 41 | SO | CH$_2$ | 1 | 3-methoxyphenyl | CH$_3$ | CH$_3$ | |
| 42 | SO | CH$_2$ | 1 | 4-methoxyphenyl | CH$_3$ | CH$_3$ | |
| 43 | SO | CH$_2$ | 1 | 2-trifluoromethylphenyl | CH$_3$ | CH$_3$ | |
| 44 | SO | CH$_2$ | 1 | 3-trifluoromethylphenyl | CH$_3$ | CH$_3$ | |
| 45 | SO | CH$_2$ | 1 | 4-trifluoromethylphenyl | CH$_3$ | CH$_3$ | |
| 46 | SO | CH$_2$ | 1 | 2,4-dichlorophenyl | CH$_3$ | CH$_3$ | |
| 47 | SO | CH$_2$ | 1 | 3,4-dichlorophenyl | CH$_3$ | CH$_3$ | |
| 48 | SO | CH$_2$ | 1 | 2-chloro, 6-fluorophenyl | CH$_3$ | CH$_3$ | |
| 49 | SO | CH$_2$ | 1 | 3,4-dimethylphenyl | CH$_3$ | CH$_3$ | |
| 50 | SO | CH$_2$CH$_2$ | 1 | phenyl | CH$_3$ | CH$_3$ | |
| 51 | SO | CH$_2$CH$_2$CH$_2$ | 1 | phenyl | CH$_3$ | CH$_3$ | |
| 52 | SO | CH$_2$CH$_2$CH$_2$CH$_2$ | 1 | 4-chlorophenyl | CH$_3$ | CH$_3$ | |
| 53 | SO | — | 0 | 1-naphthyl | CH$_3$ | CH$_3$ | |
| 54 | SO | — | 0 | 2-naphthyl | CH$_3$ | CH$_3$ | |
| 55 | SO | — | 0 | 3-phenandrenyl | CH$_3$ | CH$_3$ | |
| 56 | SO | — | 0 | 8-quinolinyl | CH$_3$ | CH$_3$ | |

TABLE 2-continued

Structure: R³—(Y)ₘ—X—CH₂—(phenyl)—C(=N—OR²)—CO₂R¹

| No. | X | (Y)ₘ | m | R³ | R¹ | R² | IR (cm⁻¹) |
|---|---|---|---|---|---|---|---|
| 57 | SO | — | 0 | phenyl | CH₃ | CH₃ | |
| 58 | SO | — | 0 | 2-chlorophenyl | CH₃ | CH₃ | 1729, 1461, 1438, 1323, 1217, 1169, 1067, 1047, 1017, 778 |
| 59 | SO | — | 0 | 3-chlorophenyl | CH₃ | CH₃ | |
| 60 | SO | — | 0 | 4-chlorophenyl | CH₃ | CH₃ | |
| 61 | SO | — | 0 | 2-bromophenyl | CH₃ | CH₃ | |
| 62 | SO | — | 0 | 3-bromophenyl | CH₃ | CH₃ | |
| 63 | SO | — | 0 | 4-bromophenyl | CH₃ | CH₃ | |
| 64 | SO | — | 0 | 2-fluorophenyl | CH₃ | CH₃ | |
| 65 | SO | — | 0 | 3-fluorophenyl | CH₃ | CH₃ | |
| 66 | SO | — | 0 | 4-fluorophenyl | CH₃ | CH₃ | |
| 67 | SO | — | 0 | 2-methylphenyl | CH₃ | CH₃ | 110–115° C. |
| 68 | SO | — | 0 | 3-methylphenyl | CH₃ | CH₃ | |
| 69 | SO | — | 0 | 4-methylphenyl | CH₃ | CH₃ | |
| 70 | SO | — | 0 | 2-ethylphenyl | CH₃ | CH₃ | |
| 71 | SO | — | 0 | 3-ethylphenyl | CH₃ | CH₃ | |
| 72 | SO | — | 0 | 4-ethylphenyl | CH₃ | CH₃ | |
| 73 | SO | — | 0 | 2-isopropylphenyl | CH₃ | CH₃ | |
| 74 | SO | — | 0 | 3-isopropylphenyl | CH₃ | CH₃ | |
| 75 | SO | — | 0 | 4-isopropylphenyl | CH₃ | CH₃ | |
| 76 | SO | — | 0 | 2-tert-butylphenyl | CH₃ | CH₃ | |
| 77 | SO | — | 0 | 3-tert-butylphenyl | CH₃ | CH₃ | |
| 78 | SO | — | 0 | 4-tert-butylphenyl | CH₃ | CH₃ | |
| 79 | SO | — | 0 | 4-butylphenyl | CH₃ | CH₃ | |
| 80 | SO | — | 0 | 4-hexylphenyl | CH₃ | CH₃ | |
| 81 | SO | — | 0 | 4-nonylphenyl | CH₃ | CH₃ | |
| 82 | SO | — | 0 | 4-decylphenyl | CH₃ | CH₃ | |
| 83 | SO | — | 0 | 2-methoxyphenyl | CH₃ | CH₃ | |
| 84 | SO | — | 0 | 3-methoxyphenyl | CH₃ | CH₃ | |
| 85 | SO | — | 0 | 4-methoxyphenyl | CH₃ | CH₃ | |
| 86 | SO | — | 0 | 2-trifluoromethylphenyl | CH₃ | CH₃ | |
| 87 | SO | — | 0 | 3-trifluoromethylphenyl | CH₃ | CH₃ | |
| 88 | SO | — | 0 | 4-trifluoromethylphenyl | CH₃ | CH₃ | |
| 89 | SO | — | 0 | 4-formylphenyl | CH₃ | CH₃ | |
| 90 | SO | — | 0 | 2-nitrophenyl | CH₃ | CH₃ | |
| 91 | SO | — | 0 | 3-nitrophenyl | CH₃ | CH₃ | |
| 92 | SO | — | 0 | 4-nitrophenyl | CH₃ | CH₃ | |
| 93 | SO | — | 0 | 2,5-dichlorophenyl | CH₃ | CH₃ | |
| 94 | SO | — | 0 | 2,6-dichlorophenyl | CH₃ | CH₃ | |
| 95 | SO | — | 0 | 3,4-dichlorophenyl | CH₃ | CH₃ | |
| 96 | SO | — | 0 | 2,3-dichlorophenyl | CH₃ | CH₃ | |
| 97 | SO | — | 0 | 2,4-dichlorophenyl | CH₃ | CH₃ | |
| 98 | SO | — | 0 | 3,5-dichlorophenyl | CH₃ | CH₃ | |
| 99 | SO | — | 0 | 2,3,4-trichlorophenyl | CH₃ | CH₃ | |
| 100 | SO | — | 0 | 2,4,5-trichlorophenyl | CH₃ | CH₃ | |
| 101 | SO | — | 0 | 2,4,6-trichlorophenyl | CH₃ | CH₃ | |
| 102 | SO | — | 0 | 2,3,4,6-tetrachlorophenyl | CH₃ | CH₃ | |
| 103 | SO | — | 0 | 2,3,4,5,6-pentachlorophenyl | CH₃ | CH₃ | |
| 104 | SO | — | 0 | 2,3,4,5-tetrafluorophenyl | CH₃ | CH₃ | |
| 105 | SO | — | 0 | 2,3,5,6-tetrafluorophenyl | CH₃ | CH₃ | |
| 106 | SO | — | 0 | 2,3,4,5,6-pentafluorophenyl | CH₃ | CH₃ | |
| 107 | SO | — | 0 | 2-chloro, 4-fluorophenyl | CH₃ | CH₃ | |
| 108 | SO | — | 0 | 3-chloro, 4-fluorophenyl | CH₃ | CH₃ | |
| 109 | SO | — | 0 | 2-chloro, 6-methylphenyl | CH₃ | CH₃ | |
| 110 | SO | — | 0 | 4-chloro, 2-methylphenyl | CH₃ | CH₃ | |
| 111 | SO | — | 0 | 2,4-dichloro, 5-methylphenyl | CH₃ | CH₃ | |
| 112 | SO | — | 0 | 4-chloro, 2,5-dimethylphenyl | CH₃ | CH₃ | |
| 113 | SO | — | 0 | 4-bromo, 3-methylphenyl | CH₃ | CH₃ | |
| 114 | SO | — | 0 | 3,5-bistrifluoromethylphenyl | CH₃ | CH₃ | |
| 115 | SO | — | 0 | 2,5-dimethylphenyl | CH₃ | CH₃ | |
| 116 | SO | — | 0 | 2,4-dimethylphenyl | CH₃ | CH₃ | |
| 117 | SO | — | 0 | 2,5-dimethylphenyl | CH₃ | CH₃ | |
| 118 | SO | — | 0 | 2,6-dimethylphenyl | CH₃ | CH₃ | |
| 119 | SO | — | 0 | 3,4-dimethylphenyl | CH₃ | CH₃ | |
| 120 | SO | — | 0 | 3,5-dimethylphenyl | CH₃ | CH₃ | |
| 121 | SO | — | 0 | 2,4,5-trimethylphenyl | CH₃ | CH₃ | |
| 122 | SO | — | 0 | 2,6-diethylphenyl | CH₃ | CH₃ | |
| 123 | SO | — | 0 | 2,4-di-tert.-butylphenyl | CH₃ | CH₃ | |
| 124 | SO | — | 0 | 2,5-dimethoxyphenyl | CH₃ | CH₃ | |
| 125 | SO | — | 0 | 3,4-dimethoxyphenyl | CH₃ | CH₃ | |
| 126 | SO | — | 0 | 2-methyl, 4-tert.-butylphenyl | CH₃ | CH₃ | |
| 127 | SO | — | 0 | 2-methoxycarbonylphenyl | CH₃ | CH₃ | |

TABLE 2-continued

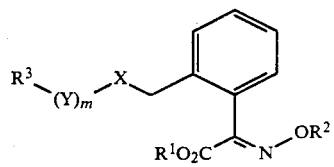

| No. | X | (Y)$_m$ | m | R$^3$ | R$^1$ | R$^2$ | IR (cm$^{-1}$) |
|---|---|---|---|---|---|---|---|
| 128 | SO | — | 0 | 2-ethoxycarbonylphenyl | CH$_3$ | CH$_3$ | |
| 129 | SO | — | 0 | 2-propoxycarbonylphenyl | CH$_3$ | CH$_3$ | |
| 130 | SO | — | 0 | 2-butoxycarbonylphenyl | CH$_3$ | CH$_3$ | |
| 131 | SO | — | 0 | 2-cyanophenyl | CH$_3$ | CH$_3$ | |
| 132 | SO | — | 0 | 3-cyanophenyl | CH$_3$ | CH$_3$ | |
| 133 | SO | — | 0 | 4-cyanophenyl | CH$_3$ | CH$_3$ | |
| 134 | SO | — | 0 | phenyl | CH$_3$ | Et | |
| 135 | SO | — | 0 | phenyl | Et | CH$_3$ | |
| 136 | SO | — | 0 | phenyl | CH$_3$ | n-Bu | |
| 137 | SO | — | 0 | phenyl | n-Bu | n-Bu | |

TABLE 3

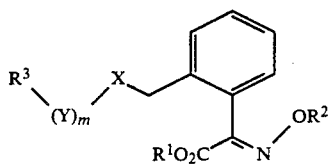

| No. | X | (Y)$_m$ | n | R$^3$ | R$^1$ | R$^2$ | IR (cm$^{-1}$) mp |
|---|---|---|---|---|---|---|---|
| 1 | SO$_2$ | CH$_2$ | 1 | H | CH$_3$ | CH$_3$ | |
| 2 | SO$_2$ | CH$_2$ | 1 | CH$_3$ | CH$_3$ | CH$_3$ | |
| 3 | SO$_2$ | CH(CH$_2$)$_2$ | 1 | CH$_3$ | CH$_3$ | CH$_3$ | |
| 4 | SO$_2$ | (CH$_2$)$_3$ | 1 | CH$_3$ | CH$_3$ | CH$_3$ | |
| 5 | SO$_2$ | (CH$_2$)$_4$ | 1 | CH$_3$ | CH$_3$ | CH$_3$ | |
| 6 | SO$_2$ | (CH$_2$)$_5$ | 1 | CH$_3$ | CH$_3$ | CH$_3$ | |
| 7 | SO$_2$ | (CH$_2$)$_6$ | 1 | CH$_3$ | CH$_3$ | CH$_3$ | |
| 8 | SO$_2$ | (CH$_2$)$_7$ | 1 | CH$_3$ | CH$_3$ | CH$_3$ | |
| 9 | SO$_2$ | (CH$_2$)$_8$ | 1 | CH$_3$ | CH$_3$ | CH$_3$ | |
| 10 | SO$_2$ | (CH$_2$)$_9$ | 1 | CH$_3$ | CH$_3$ | CH$_3$ | |
| 11 | SO$_2$ | CH(i-Pr) | 1 | CH$_3$ | CH$_3$ | CH$_3$ | |
| 12 | SO$_2$ | CH(CH$_3$) | 1 | CH$_3$ | CH$_3$ | CH$_3$ | |
| 13 | SO$_2$ | CH(Et) | 1 | CH$_3$ | CH$_3$ | CH$_3$ | |
| 14 | SO$_2$ | CH(Pr) | 1 | CH$_3$ | CH$_3$ | CH$_3$ | |
| 15 | SO$_2$ | CH$_2$ | 1 | cyclopropyl | CH$_3$ | CH$_3$ | |
| 16 | SO$_2$ | CH$_2$ | 1 | cyclohexyl | CH$_3$ | CH$_3$ | |
| 17 | SO$_2$ | — | 0 | cyclopentyl | CH$_3$ | CH$_3$ | |
| 18 | SO$_2$ | — | 0 | cyclohexyl | CH$_3$ | CH$_3$ | |
| 19 | SO$_2$ | — | 0 | cyclooctyl | CH$_3$ | CH$_3$ | |
| 20 | SO$_2$ | CH$_2$ | 1 | 1-naphthyl | CH$_3$ | CH$_3$ | |
| 21 | SO$_2$ | CH(CH$_3$) | 1 | phenyl | CH$_3$ | CH$_3$ | |
| 22 | SO$_2$ | CH$_2$ | 1 | CH=CH$_2$ | CH$_3$ | CH$_3$ | |
| 23 | SO$_2$ | CH$_2$ | 1 | C(CH$_3$)=CH$_2$ | CH$_3$ | CH$_3$ | |
| 24 | SO$_2$ | CH$_2$ | 1 | 2-chlorophenyl | CH$_3$ | CH$_3$ | |
| 25 | SO$_2$ | CH$_2$ | 1 | 3-chlorophenyl | CH$_3$ | CH$_3$ | |
| 26 | SO$_2$ | CH$_2$ | 1 | 4-chlorophenyl | CH$_3$ | CH$_3$ | |
| 27 | SO$_2$ | CH$_2$ | 1 | 2-bromophenyl | CH$_3$ | CH$_3$ | |
| 28 | SO$_2$ | CH$_2$ | 1 | 3-bromophenyl | CH$_3$ | CH$_3$ | |
| 29 | SO$_2$ | CH$_2$ | 1 | 4-bromophenyl | CH$_3$ | CH$_3$ | |
| 30 | SO$_2$ | CH$_2$ | 1 | 2-fluorophenyl | CH$_3$ | CH$_3$ | |
| 31 | SO$_2$ | CH$_2$ | 1 | 3-fluorophenyl | CH$_3$ | CH$_3$ | |
| 32 | SO$_2$ | CH$_2$ | 1 | 4-fluorophenyl | CH$_3$ | CH$_3$ | |
| 33 | SO$_2$ | CH$_2$ | 1 | 2-methylphenyl | CH$_3$ | CH$_3$ | |
| 34 | SO$_2$ | CH$_2$ | 1 | 3-methylphenyl | CH$_3$ | CH$_3$ | |
| 35 | SO$_2$ | CH$_2$ | 1 | 4-methylphenyl | CH$_3$ | CH$_3$ | |
| 36 | SO$_2$ | CH$_2$ | 1 | 4-dodecylphenyl | CH$_3$ | CH$_3$ | |
| 37 | SO$_2$ | CH$_2$ | 1 | 2-nitrophenyl | CH$_3$ | CH$_3$ | |
| 38 | SO$_2$ | CH$_2$ | 1 | 3-nitrophenyl | CH$_3$ | CH$_3$ | |
| 39 | SO$_2$ | CH$_2$ | 1 | 4-nitrophenyl | CH$_3$ | CH$_3$ | |
| 40 | SO$_2$ | CH$_2$ | 1 | 2-methoxyphenyl | CH$_3$ | CH$_3$ | |
| 41 | SO$_2$ | CH$_2$ | 1 | 3-methoxyphenyl | CH$_3$ | CH$_3$ | |
| 42 | SO$_2$ | CH$_2$ | 1 | 4-methoxyphenyl | CH$_3$ | CH$_3$ | |
| 43 | SO$_2$ | CH$_2$ | 1 | 2-trifluoromethylphenyl | CH$_3$ | CH$_3$ | |
| 44 | SO$_2$ | CH$_2$ | 1 | 3-trifluoromethylphenyl | CH$_3$ | CH$_3$ | |
| 45 | SO$_2$ | CH$_2$ | 1 | 4-trifluoromethylphenyl | CH$_3$ | CH$_3$ | |
| 46 | SO$_2$ | CH$_2$ | 1 | 2,4-dichlorophenyl | CH$_3$ | CH$_3$ | |
| 47 | SO$_2$ | CH$_2$ | 1 | 3,4-dichlorophenyl | CH$_3$ | CH$_3$ | |

TABLE 3-continued

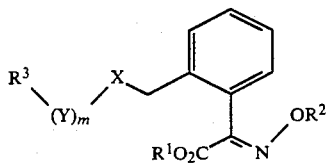

| No. | X | (Y)$_m$ | n | R$^3$ | R$^1$ | R$^2$ | IR (cm$^{-1}$) mp |
|---|---|---|---|---|---|---|---|
| 48 | SO$_2$ | CH$_2$ | 1 | 2-chloro, 6-fluorophenyl | CH$_3$ | CH$_3$ | |
| 49 | SO$_2$ | CH$_2$ | 1 | 3,4-dimethylphenyl | CH$_3$ | CH$_3$ | |
| 50 | SO$_2$ | CH$_2$CH$_2$ | 1 | phenyl | CH$_3$ | CH$_3$ | |
| 51 | SO$_2$ | CH$_2$CH$_2$CH$_2$ | 1 | phenyl | CH$_3$ | CH$_3$ | |
| 52 | SO$_2$ | CH$_2$CH$_2$CH$_2$CH$_2$ | 1 | 4-chlorophenyl | CH$_3$ | CH$_3$ | |
| 53 | SO$_2$ | — | 0 | 1-naphthyl | CH$_3$ | CH$_3$ | |
| 54 | SO$_2$ | — | 0 | 2-naphthyl | CH$_3$ | CH$_3$ | |
| 55 | SO$_2$ | — | 0 | 3-phenandrenyl | CH$_3$ | CH$_3$ | |
| 56 | SO$_2$ | — | 0 | 8-quinolinyl | CH$_3$ | CH$_3$ | |
| 57 | SO$_2$ | — | 0 | phenyl | CH$_3$ | CH$_3$ | |
| 58 | SO$_2$ | — | 0 | 2-chlorophenyl | CH$_3$ | CH$_3$ | 143–150° C. |
| 59 | SO$_2$ | — | 0 | 3-chlorophenyl | CH$_3$ | CH$_3$ | 126–130° C. |
| 60 | SO$_2$ | — | 0 | 4-chlorophenyl | CH$_3$ | CH$_3$ | |
| 61 | SO$_2$ | — | 0 | 2-bromophenyl | CH$_3$ | CH$_3$ | |
| 62 | SO$_2$ | — | 0 | 3-bromophenyl | CH$_3$ | CH$_3$ | |
| 63 | SO$_2$ | — | 0 | 4-bromophenyl | CH$_3$ | CH$_3$ | |
| 64 | SO$_2$ | — | 0 | 2-fluorophenyl | CH$_3$ | CH$_3$ | |
| 65 | SO$_2$ | — | 0 | 3-fluorophenyl | CH$_3$ | CH$_3$ | |
| 66 | SO$_2$ | — | 0 | 4-fluorophenyl | CH$_3$ | CH$_3$ | |
| 67 | SO$_2$ | — | 0 | 2-methylphenyl | CH$_3$ | CH$_3$ | 124–127° C. |
| 68 | SO$_2$ | — | 0 | 3-methylphenyl | CH$_3$ | CH$_3$ | |
| 69 | SO$_2$ | — | 0 | 4-methylphenyl | CH$_3$ | CH$_3$ | |
| 70 | SO$_2$ | — | 0 | 2-ethylphenyl | CH$_3$ | CH$_3$ | |
| 71 | SO$_2$ | — | 0 | 3-ethylphenyl | CH$_3$ | CH$_3$ | |
| 72 | SO$_2$ | — | 0 | 4-ethylphenyl | CH$_3$ | CH$_3$ | |
| 73 | SO$_2$ | — | 0 | 2-isopropylphenyl | CH$_3$ | CH$_3$ | |
| 74 | SO$_2$ | — | 0 | 3-isopropylphenyl | CH$_3$ | CH$_3$ | |
| 75 | SO$_2$ | — | 0 | 4-isopropylphenyl | CH$_3$ | CH$_3$ | |
| 76 | SO$_2$ | — | 0 | 2-tert-butylphenyl | CH$_3$ | CH$_3$ | |
| 77 | SO$_2$ | — | 0 | 3-tert-butylphenyl | CH$_3$ | CH$_3$ | |
| 78 | SO$_2$ | — | 0 | 4-tert-butylphenyl | CH$_3$ | CH$_3$ | |
| 79 | SO$_2$ | — | 0 | 4-butylphenyl | CH$_3$ | CH$_3$ | |
| 80 | SO$_2$ | — | 0 | 4-hexylphenyl | CH$_3$ | CH$_3$ | |
| 81 | SO$_2$ | — | 0 | 4-nonylphenyl | CH$_3$ | CH$_3$ | |
| 82 | SO$_2$ | — | 0 | 4-decylphenyl | CH$_3$ | CH$_3$ | |
| 83 | SO$_2$ | — | 0 | 2-methoxyphenyl | CH$_3$ | CH$_3$ | |
| 84 | SO$_2$ | — | 0 | 3-methoxyphenyl | CH$_3$ | CH$_3$ | |
| 85 | SO$_2$ | — | 0 | 4-methoxyphenyl | CH$_3$ | CH$_3$ | |
| 86 | SO$_2$ | — | 0 | 2-trifluoromethylphenyl | CH$_3$ | CH$_3$ | |
| 87 | SO$_2$ | — | 0 | 3-trifluoromethylphenyl | CH$_3$ | CH$_3$ | |
| 88 | SO$_2$ | — | 0 | 4-trifluoromethylphenyl | CH$_3$ | CH$_3$ | |
| 89 | SO$_2$ | — | 0 | 4-formylphenyl | CH$_3$ | CH$_3$ | |
| 90 | SO$_2$ | — | 0 | 2-nitrophenyl | CH$_3$ | CH$_3$ | |
| 91 | SO$_2$ | — | 0 | 3-nitrophenyl | CH$_3$ | CH$_3$ | |
| 92 | SO$_2$ | — | 0 | 4-nitrophenyl | CH$_3$ | CH$_3$ | |
| 93 | SO$_2$ | — | 0 | 2,5-dichlorophenyl | CH$_3$ | CH$_3$ | |
| 94 | SO$_2$ | — | 0 | 2,6-dichlorophenyl | CH$_3$ | CH$_3$ | |
| 95 | SO$_2$ | — | 0 | 3,4-dichlorophenyl | CH$_3$ | CH$_3$ | |
| 96 | SO$_2$ | — | 0 | 2,3-dichlorophenyl | CH$_3$ | CH$_3$ | |
| 97 | SO$_2$ | — | 0 | 2,4-dichlorophenyl | CH$_3$ | CH$_3$ | |
| 98 | SO$_2$ | — | 0 | 3,5-dichlorophenyl | CH$_3$ | CH$_3$ | |
| 99 | SO$_2$ | — | 0 | 2,3,4-trichlorophenyl | CH$_3$ | CH$_3$ | |
| 100 | SO$_2$ | — | 0 | 2,4,5-trichlorophenyl | CH$_3$ | CH$_3$ | |
| 101 | SO$_2$ | — | 0 | 2,4,6-trichlorophenyl | CH$_3$ | CH$_3$ | |
| 102 | SO$_2$ | — | 0 | 2,3,4,6-tetrachlorophenyl | CH$_3$ | CH$_3$ | |
| 103 | SO$_2$ | — | 0 | 2,3,4,5,6-pentachlorophenyl | CH$_3$ | CH$_3$ | |
| 104 | SO$_2$ | — | 0 | 2,3,4,5-tetrafluorophenyl | CH$_3$ | CH$_3$ | |
| 105 | SO$_2$ | — | 0 | 2,3,5,6-tetrafluorophenyl | CH$_3$ | CH$_3$ | |
| 106 | SO$_2$ | — | 0 | 2,3,4,5,6-pentafluorophenyl | CH$_3$ | CH$_3$ | |
| 107 | SO$_2$ | — | 0 | 2-chloro, 4-fluorophenyl | CH$_3$ | CH$_3$ | |
| 108 | SO$_2$ | — | 0 | 3-chloro, 4-fluorophenyl | CH$_3$ | CH$_3$ | |
| 109 | SO$_2$ | — | 0 | 2-chloro, 6-methylphenyl | CH$_3$ | CH$_3$ | |
| 110 | SO$_2$ | — | 0 | 4-chloro, 2-methylphenyl | CH$_3$ | CH$_3$ | |
| 111 | SO$_2$ | — | 0 | 2,4-dichloro, 5-methylphenyl | CH$_3$ | CH$_3$ | |
| 112 | SO$_2$ | — | 0 | 4-chloro, 2,5-dimethylphenyl | CH$_3$ | CH$_3$ | |
| 113 | SO$_2$ | — | 0 | 4-bromo, 3-methylphenyl | CH$_3$ | CH$_3$ | |
| 114 | SO$_2$ | — | 0 | 3,5-bistrifluoromethylphenyl | CH$_3$ | CH$_3$ | |
| 115 | SO$_2$ | — | 0 | 2,5-dimethylphenyl | CH$_3$ | CH$_3$ | |
| 116 | SO$_2$ | — | 0 | 2,4-dimethylphenyl | CH$_3$ | CH$_3$ | |
| 117 | SO$_2$ | — | 0 | 2,5-dimethylphenyl | CH$_3$ | CH$_3$ | |
| 118 | SO$_2$ | — | 0 | 2,6-dimethylphenyl | CH$_3$ | CH$_3$ | |

TABLE 3-continued

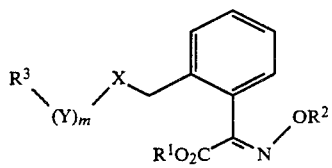

| No. | X | (Y)$_m$ | n | R$^3$ | R$^1$ | R$^2$ | IR (cm$^{-1}$) mp |
|---|---|---|---|---|---|---|---|
| 119 | SO$_2$ | — | 0 | 3,4-dimethylphenyl | CH$_3$ | CH$_3$ | |

Generally speaking the nove compounds are extremely effective on a broad spectrum of phytopathogenic fungi, in particular those from the Ascomycetes and Basidiomycetes classes. Some of them have a systemic action and can be used as foliar and soil fungicides.

The fungicidal compounds are of particular interest for controlling a large number of fungi in various crops or their seeds especially wheat, rye, barley, oats, rice. Indian corn. lawns, cotton, soybeans, coffee sugar cane, fruit and ornamentals in horticulture and viticulture, and in vegetables such as cucumbers, beans and cucurbits.

The novel compounds are particularly useful for controlling the following plant diseases:
*Erysiphe graminis* in cereals,
*Erysiphe cichoracearum* and *Sphaerotheca fuliginea* in cucurbits,
*Podosphaera leucotricha* in apples
*Uncinula necator* in vines,
Puccinia species in cereals,
Rhizoctonia species in cotton and lawns,
Ustilago species in cereals and suqar cane,
Venturia inaequalis (scah) in apples
Helminthosporium species in cereals,
*Septoria nodorum* in wheat
Botrytis cinerea (gray mold) in strawberries and grapes,
*Cercospora arachidicola* in groundnuts
*Pseudocercosporella herpotrichoides* in wheat and barley.
*Pyricularia oryzae* in rice,
*PhytoPhthora infestans* in potatoes and tomatoes,
Fusarium and verticillium species in various plants,
*Plasmopara viticola* in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers with or without the use of emulsifiers and dispersants; if water is used as solvent, it is also possible to employ other organic solvents as auxiliary solvents. Suitable auxillaries for this purpose are solvents such as aromatics (e.g. xylene). chlorinated aromatics (e.g., chlorobenzenes), paraffins (e.g., crude oil fractions), alcohols (e.g., methanol butanol) ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin sulfite waste liquors and methylcellulose.

The fungicidal agents generally contaln from 0.1to 95, and preferably from 0.5 to 90 wt% of active ingredient. The application rates are from 0.02 to 3 kg or more of active ingredient per hectare, depending on the type of effect desired. The novel compounds may also be used for protecting materials for example against paecllomyces variotii.

The agents and the ready-to-use formulations prepared from them, such as solutions. emulsions, suspensions, powders, dusts, pastes and granules, are applied in conventional manner, for example by spraying, atomizing, dusting scattering, dressing or watering.

Examples of formulations are given below.

I. 20 parts by weight of compound no. 57 is mixed with 10 parts by weight of N-methyl-α-pyrrolidone. A mixture is obtained which is suitable for application in the form of very fine drops.

II. 20 parts by weight of compound no. 58 is dissolved in a mixture consisting of 80 parts by weight of xylene, 10 parts by weight of the adduct of 8 to 10 moles of ethylene oxide and 1 mole of oleic acid-N-monoethanolamide 5 parts by weiqht of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained. III. 20 parts by weight of compound no. 59 is dissolved in a mixture consistlng of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 67 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 57 is well mixed with 3 parts by weight of the sodium salt of diisobutylnaphthalene-α-sulfonic acid, 10 parts by weight of the sodium salt of a lignin-sulfonic acid obtained from a sulfite waste liquor. and 7 parts by weight of powdered silica gel, and triturated in a hammer mill.

By uniformly distributing the mixture in water, a spray liquor is obtained.

VI. 3 parts by weight of compound no. 58 is intimately mixed with 97 parts by weight of particulate kaolin. A dust is obtained containing 3% by weight of the active ingredient.

VII. 30 parts by weight of compound no. 67 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 67 is intimately mixed with 10 parts by weight of the sodium salt of a phenolsulfonic acid-ureaformaldehyde condensate 2 parts of silica gel and 48 parts of water to give a stable aqueous dispersion. Dilution in water gives an aqueous dispersion.

IX. 20 parts by weight of compound no. 57 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in an increase in the fungicidal spectrum.

The following list of fungicides with which the novel compounds may be combined is intended to illustrate possible combinations but not to impose any restrictions.

Examples of fungicides which may be combined with the novel compounds are:
sulfur,
dithiocarbamates and their derivatives, such as
ferric dimethyldithiocarbamate.
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithiocarbamate and
N,N'-polypropylenebisthiocarbamyl disulfide;
nitro derivatives such as
dinitro(1-methylheptyl)-phenyl crotonate,
2-sec-butyl-4,6-dinitrophenyl 3,3-dimethylacrylate.
2-sec-butyl-4,6-dinitrophenyl isopropylcarbonate and
diisopropyl 5-nitroisophthalate;
heterocyclic substances such as
2-heptadecylimidazol-2-yl acetate,
2,4-dichloro-6-(o-chloroanilino)-s-triazine
0,0-diethyl phthalimidophosphonothioate,
5-amino-1-[-bis-ldimethylamino)-phosphinyl)-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-fur-2-yl-benzimidazole,
2-thiazol-4-yl)benzimidazole,
N-(1,1,2,2-tetrachloroethylthio)-tetrahydrophthalimide,
N-trichloromethylthiotetrahydrophthalimide.
N-trichloromethylthiophthalimide,
N-dichlorofluoromethylthio-N',N'-dimethyl-N-phenylsulfuric acid diamide,
5-ethoxy-3-trichloromethyl-1,2,3-thiadiazole
2-thiocyanatomethylthiobenzothiazole,
1,4-dichloro-2,5-dimethoxybenzene
4-(2-chlorophenylhydrazono-3-methyl-5-isoxazolone
2-thiopyridine 1-oxide,
8-hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-meihylfuran-3-carboxanilide,
2,5-dimethylfuran-3-carboxanilide,
2,4,5-trimeihylfuran-3-carboxanilide
2,5-dimethyl-N-cyclohexylfuran-3-carboxamide,
N-cyclohexyl-N-methoxy-2,5-diethylfuran-3-carboxamide,
2-methylbenzanilide
2-iodobenzanilide,
N-formyl-N-morpholine-2,2,2-trichloroethylacetal,
piperazine-1,4-diylbis-1-(2,2,2-trichloroethyl-formamide,
1-(3,4-dichloroanilino)-1-formylamino-2,2,2-trichloroethane,
2,6-dimethyl-N-tridecylmorpholine and its salts
2,6-dimethyl-N-cyclododecylmorpholine and its salts,
N-[3-(p-tert.-butylphenyl)-2-methylpropyl]-cis-2,6-dlmethylmorpholine,
N-[3-(p-tert.-butylphenyl)-2-meihylpropyl]-plperldine,
1-[2-(2,4-dichlorophenyl-4-ethyl-1,3-dioxolan-2-ylethyl)-1H-1,2,4-triazole,
1-[2-(2,4-dichlorophenyl)-4-n-propyl-1,3-dioxolan-2-ylethyl)-1H-1,2,4-triazole,
N-(n-propyl)-N-(2,4,6-trichlorophenoxyethyl)-N'-imidazolyl-urea,
1-(4-chlorophenoxy)-3,3-dimethyl-1-1H-1,2,4-triazol-1-yl-butan-2-one,
1-(b 4-chlorophenoxy)-3,3-dimethyl-1-(1H-1,2,4-triazol-1-yl)-butan-2-ol.
1-(4-phenylphenoxy)-3,3-dimethyl-1-1H-1,2,4-triazol-1-yl-2-butanol.
α(2-chlorophenyl-α-4-chlorophenyl-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-meihoxycarbonyl-2-thioureido)-benzene,
and various fungicides such as
dodecylguanidine acetate,
3-[3-(3,5-dimethyl-2-oxycyclohexyl)-2-hydroxyethyl]-glutaramide,
hexachlorobenzene,
DL-methyl-N-(2,6-dimethylphenyl)-N-fur-2-yl alanate,
methyl DL-N-(2,6-dimethylphenyl-N-2,-methoxyacetyl)-alanate,
N-(2,6-dimethylphenyl)-N-chloroacetyl-DL-2-aminobutyrolactone.
methyl DL-N-2,6-dimethylphenyl)-N-(phenylacetyl)-alanate.
5-methyl-5-vlnyl-3-(3,5-dichlorophenyl)-2,4-dioxo-1,3-oxazolidine, 3-[3,5-dichlorophenyl]-5-methyl-5-methoxymethyl-1,3-oxazolidine-2,4-dione, 3-3,5-dichlorophenyl)-1-isopropylcarbamylhydantoin.

N-3,5-dichlorophenyl)-1,2-dimethylcyclopropane-1,2-dicarboximide, 2-cyano-[N-(ethylaminocarbonyl-2-methoximino)-acetamide, 1-[2-(2,4-dichlorophenyl)-pentyl]-1H-1,2,4-triazole, 2,4-difluoro-α-(b 1H-1,2,4-trazol-1-ylmethyl)-benzhydryl alcohol, N-3-chloro-2,6-dinitro-4-trifluoromethylphenyl)-5-trifluoromethyl-3-chloro-2-aminopyridine, and 1-((bis-4-fluorophenyl-methylsilyl)-methyl)-1H-1,2,4-triazole.

USE EXAMPLE

For comparison purposes. prior art active ingredient 2-(phenyloxymethyl)-phenylglyoxalic acid-O-methyloxime (A) disclosed in EP 253,213 was used.

Action on *Pyrenophora teres*

Barley seedlings of the "Igri" variety were sprayed to runoff at the two-leaf stage with aqueous suspensions consisting (dry basis of 80% of active ingredient and 20% of emulsifier. After 24 hours the plants were inoculated with a spore suspension of the fungus *Pyrenophora teres*, and set up for 48 hours in a high-humidity climatic cabinet at 18° C. The plants were then cultivated for a further 5 days in the greenhouse at 20° to 22° C. and a relative humidity of 70%. The extent of fungus spread was then assessed.

The results show that active ingredients 57. 58, 5g and 67, applied as 0.05wt% spray liquors have a better fungicidal action (100%) than prior art active ingredient A (65%).

We claim:

1. Oxime ether derivatives of the formula

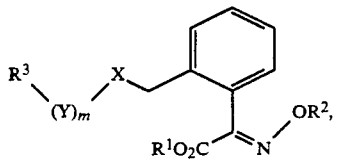

where $R^1$ and $R^2$ are each hydrogen or $C_1$–$C_5$-alkyl, X is S, SO or $SO_2$, $R^3$ is hydrogen, or a $C_3$–$C_8$-cycloalkyl, phenyl, naphthyl, or phenanthrenyl radical, these radicals being unsubstituted or substituted by cyano, nitro, formyl, $C_1$–$C_4$-alkyl, $C_1$–$C_4$-alkoxy, $C_1$–$C_2$-haloalkyl, aryl or $C_1$–$C_4$-alkoxycarbonyl, y is a straight-chain or branched alkylene, alkenylene or alkynylene radical, and m is 0 or 1.

2. A process for combating fungi, wherein the fungi, or the materials, plants, seed or soil threatened by fungus attack are treated with a fungicidally effective amount of an oxime ether derivative of the formula

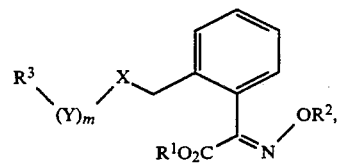

where $R^1$ and $R^2$ are each hydrogen or $C_1$–$C_5$-alkyl, X is S, SO or $SO_2$, $R^3$ is hydrogen, or a $C_3$–$C_8$-cycloalkyl, phenyl, naphthyl, or phenanthrenyl radical, these radicals being unsubstituted or substituted by halogen, cyano, nitro, formyl, $C_1$–$C_{10}$-alkyl, $C_1$–$C_4$-alkoxy, $C_1$–$C_2$-halo-alkyl, aryl or $C_1$–$C_4$-alkoxycarbonyl, Y is a straight-chain or branched alkylene, alkenyene or alkynlene radical and m is 0 or 1.

3. A fungicide containing an inert carrier and a fungicidally effective amount of an oxime ether derivative of the formula

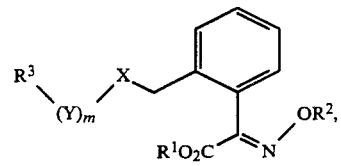

where $R^1$ and $R^2$ are each hydrogen or $C_1$–$C_5$-alkyl, X is S, SO or $SO_2$. $R^3$ is hydrogen, or a $C_3$–$C_8$-cycloalkyl, phenyl, naphthyl, or phenanthrenyl radical, these radicals being unsubstituted or substituted by halogen, cyano, nitro, formyl, $C_1$–$C_{10}$-alkyl, $C_1$–$C_4$-alkoxy, $C_1$–$C_2$-haloalkyl, aryl or $C_1$–$C_4$-alkoxycarbonyl, Y is a straight-chain or branched alkylene, alkenylene or alkynylene radical, and m is 0 or 1.

4. A compound as set forth in claim 1, where $R^1$ and $R^2$ are methyl, X is S, $R^3$ is phenyl and $Y_m$ is methylene.

5. A compound as set forth in claim 1, where $R^1$ and $R^2$ are methyl, X is S, $R^3$ is 2-chorophenyl and $Y_m$ is methylene.

6. A compound as set forth in claim 1, where $R^1$ and $R^2$ are methyl, X is S, $R^3$ is 3-chlorophenyl and $Y_m$ is methylene.

7. A compound as set forth in claim 1, where $R^1$ and $R^2$ are methyl, X is S, $R^3$ is 2-methylphenyl and $Y_m$ is methylene.

* * * * *